(12) United States Patent
Kerns (10) Patent No.: US 11,904,122 B1
(45) Date of Patent: Feb. 20, 2024

(54) DISPOSABLE PASS THROUGH DILATOR AND METHOD OF USE

(71) Applicant: Roxana Belciu Kerns, West Palm Beach, FL (US)

(72) Inventor: Roxana Belciu Kerns, West Palm Beach, FL (US)

(*) Notice: Subject to any disclaimer, the term of this patent is extended or adjusted under 35 U.S.C. 154(b) by 82 days.

(21) Appl. No.: 17/481,070

(22) Filed: Sep. 21, 2021

Related U.S. Application Data (60) Provisional application No. 63/224,220, filed on Jul. 21, 2021, provisional application No. 63/196,873, filed on Jun. 4, 2021.

(51) Int. Cl.
*A61M 29/00* (2006.01)

(52) U.S. Cl.
CPC ..... *A61M 29/00* (2013.01); *A61M 2210/1433* (2013.01)

(58) Field of Classification Search
CPC ........ A61F 2/012; A61F 2/0105; A61F 2/014; A61F 2/011; A61F 2002/016; A61F 2002/018; A61M 25/0147; A61M 25/0068; A61B 17/221; A61B 2017/2212; A61B 2017/2215
See application file for complete search history.

(56) References Cited

U.S. PATENT DOCUMENTS

| | | | |
|---|---|---|---|
| 3,431,910 A | 3/1969 | Kokx | |
| 3,706,311 A | 12/1972 | Kokx et al. | |
| 3,902,493 A | 9/1975 | Baier et al. | |
| 4,237,893 A * | 12/1980 | Michaels | A61M 29/02 128/839 |
| 5,782,745 A * | 7/1998 | Benderev | A61H 19/40 128/DIG. 25 |
| 2003/0216770 A1* | 11/2003 | Persidsky | A61B 17/3439 606/198 |
| 2007/0282161 A1* | 12/2007 | Ferguson | A61F 2/0009 600/32 |
| 2008/0146872 A1 | 6/2008 | Gruber | |

(Continued)

FOREIGN PATENT DOCUMENTS

| | | | |
|---|---|---|---|
| WO | WO-2021074917 A1 * | 4/2021 | ......... A61F 13/2022 |
| WO | 2022/255897 A1 | 12/2022 | |

OTHER PUBLICATIONS

PCT International Search Report and Written Opinion of the International Searching Authority for International Application No. PCT/RO2022/050001 (published as co-pending application WO 2022/255897) dated Jul. 14, 2022.

*Primary Examiner* — Jing Rui Ou
(74) *Attorney, Agent, or Firm* — The Dobrusin Law Firm, P.C.; Daniela M. Thompson-Walters (57) ABSTRACT

A dilator includes a tubular member composed of a flexible material, the tubular member forming a channel; wires extending inwardly from an interior of the tubular member into the channel; a string attached to the wires and extending through the channel; and a handle attached to the string; pulling the handle applies force to the string; force to the string causes the string to disengage from the wires such that the wires recoil against the interior of the tubular member such that the tubular member takes on a diameter of a predetermined dimension; and the tubular member in a recoiled state provides for dilation of a canal.

20 Claims, 6 Drawing Sheets

(56) References Cited

U.S. PATENT DOCUMENTS

| | | | |
|---|---|---|---|
| 2011/0172694 A1* | 7/2011 | Ackerman | A61F 2/0027 606/192 |
| 2014/0100417 A1* | 4/2014 | Durling | A61F 6/08 600/30 |

* cited by examiner

DISPOSABLE PASS THROUGH DILATOR AND METHOD OF USE

BACKGROUND

1. Field of the Invention

The present invention relates generally to an anatomical dilator in particular cervical dilator. More specifically, the present invention describes a disposable medical device used in (gynecological but also rectal or urological) surgical procedures to dilate free of trauma stenotic anatomical orifices (uterine cervix, anal canal, urethra) and to allow passage of medical instruments inside the cavity (uterus, rectum, bladder).

2. Description of Related Art

Surgical Gynecologycal procedures refer to medical surgery or interventions on the female reproductive system. A dilator, medical (surgical) device, is used to expand a closed, stenotic or otherwise small opening or passage such as cervix, urethra, esophagus, rectum or vaginal introitus during procedure(s) or for treatment(s). The Dilators available currently in the industry are essentially metallic or plastic and have encountered several limitations. They require (re)sterilization, a process that removes, kills or deactivates all forms of life. The dilators available need additional, skilled assistance for instrumentation, a trained and skilled medical assistant or nurse which can be quite costly and not time efficient. The dilators available come in increasing sizes and require multiple instrumentation to achieve a desired opening; therefore, increased risk for trauma (require stabilization by uterine tenaculum), increased operating time and anesthetic dosage. Often times metallic dilators cannot open a closed cervix and procedures risk to be canceled after induction of anesthesia. The force exerted from the present dilators can cause trauma to cervical canal and even perforate uterus, which require additional medical treatments, hospitalization, increased cost. Other available dilators require complex and expensive methodology (eg. Balloon dilators) or and need long time to achieve a dilated state (eg. Osmotic cervical dilator or laminaria).

An objective of the present invention is to provide a Disposable dilator that allows a user to utilize it without need for re-sterilization, during gynecological but also related medical procedures that encounter a stenotic orifice that needs opening for passage of instruments or visualization. (eg rectal instrumentation, urethra instrumentation). Another objective is to provide a dilator that has a soft expandable outer structure that poses no mechanical traumatic risk to anatomical structures. Another objective is to provide a dilator with an inner metallic core that comprises a plurality of elastic wires that are restricted to expand in neutral position by a centered metallic string. The user can release the elastic wires to expand into the softer external material by simply pulling the metallic string out. The metallic string is the center piece of the invention and when triggered can activate the present invention to dilate and open the cervix or similar anatomical structures as exemplified above (urethra, anal canal). Once the elastic wires are released from the central string, the present invention provides a through-hole that allows passage of hysteroscope or other medical devices not limited to curets, suction catheter, uterine measuring devices, polyp baskets or scissors (urethroscope, rectoscope).

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

The present invention provides a disposable and pass-through anatomical (cervical) dilator. The present invention will allow users to dilate the uterine cervix (also anal canal and urethra) without trauma, without extraordinary skilled training, without need for re-sterilization, without requiring a complex operating surgical environment (hospital or ambulatory surgical center), in a time efficient and sterile medical office setting.

Figure 1:
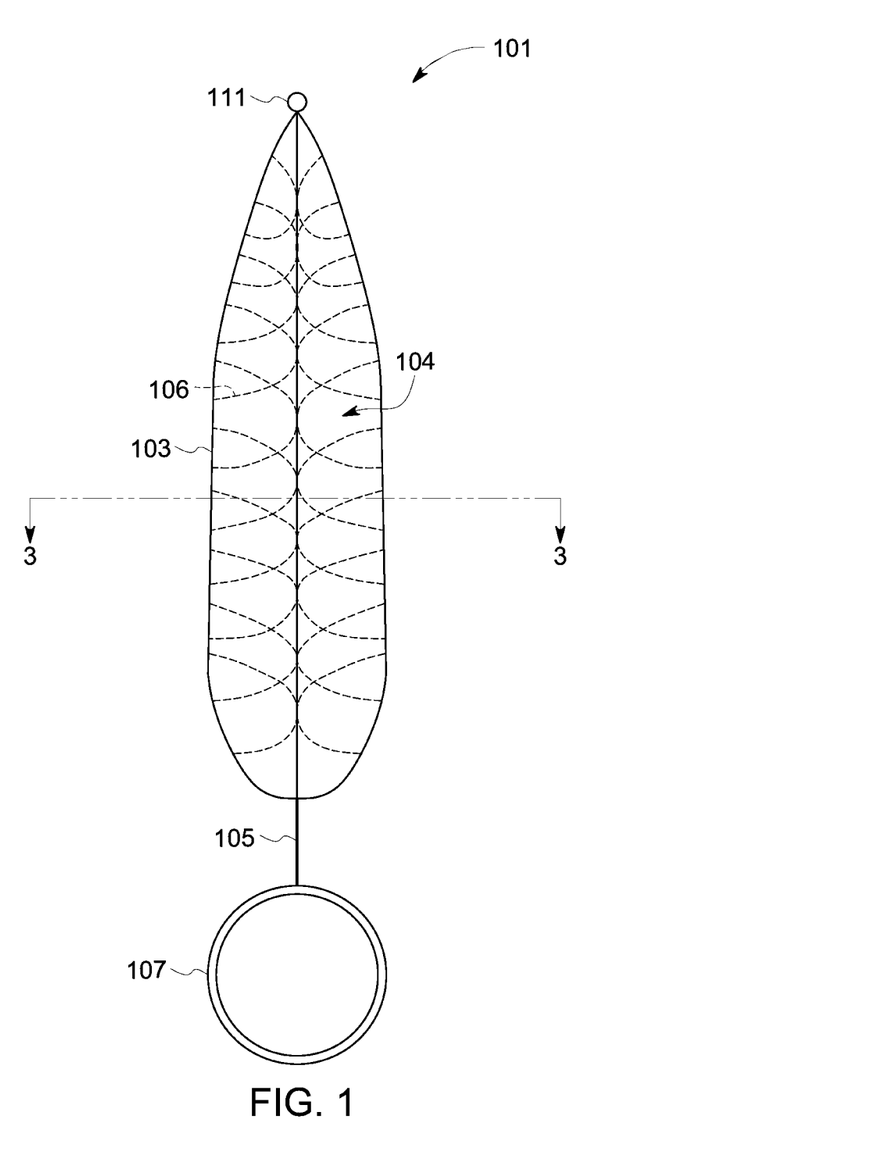
FIG. 1 is a front view of a dilator in accordance with a preferred embodiment of the present application.

In the contemplated embodiment, as shown in FIG. 1, the present invention includes a dilator 101 having the core components of a tubular member 103 that forms a channel 104 which is obstructed via a plurality of wires 106 when not in a dilated configuration (see FIG. 3) and is unobstructed by the plurality of wires 106 when in a dilated/recoiled configuration (see FIG. 5), a string 105, and a handle 107. As shown, the string 105 extends into the channel 104 and is engaged with the plurality of wires. This allows for the user to remove the string, such that the wires retract against the tubular member to provide dilation as discussed below.

Figure 2:
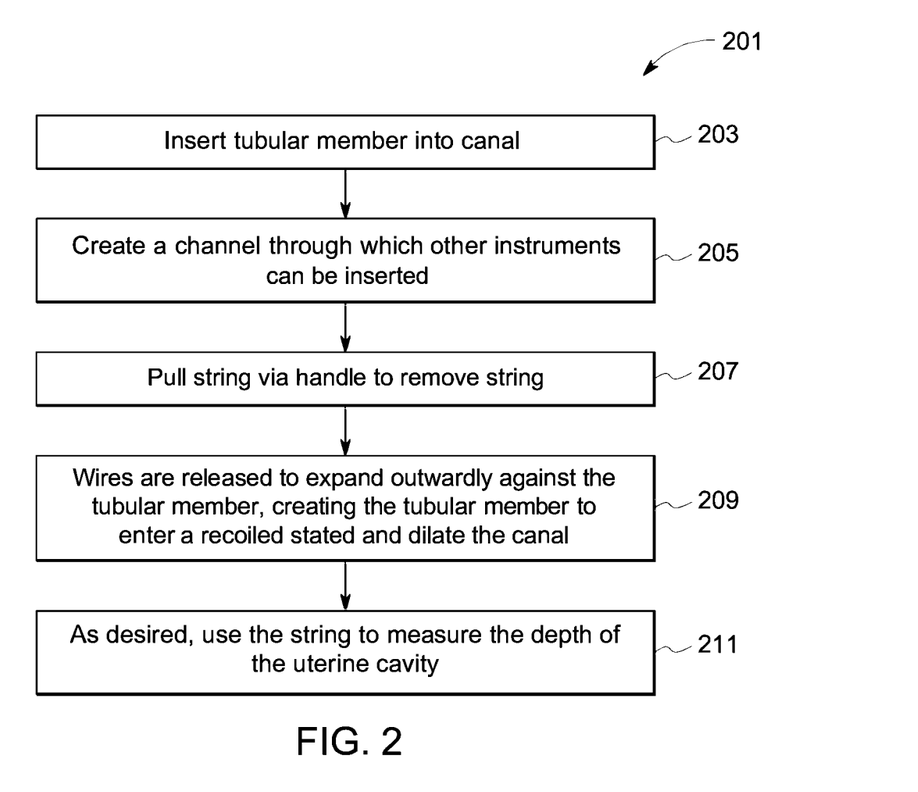
FIG. 2 is a flowchart of a method of use of the dilator of FIG. 1.

In FIG. 2, a flowchart 201 depicts a method of use of the dilator 101. During use, the tubular member 103 is inserted into a patient's cervix, cervical canal, or uterine opening (or anal canal or urethra) and provides a passageway (channel 104) for other surgical devices such as hysteroscope, a curette, a rectoscope, a suctioning catheter, polyp scissors, basket, etc., as shown with boxes 203, 205. Next, the string 105 can be pulled out to trigger the expansion and opening of the tubular member, as shown with box 207. The handle allows for the user to manipulate the string, such as to pull the string downward and out of the canal, such as to release inner metallic elastic wires 106 into expansion, as shown with box 209. This causes the wires to exert force against the interior of the tubular member to create a predetermined dimension of the tubular member within the canal and thereby dilate the canal.

Depending on the needed use, the string 105, which in the preferred embodiment is composed of reinforced blunt coil, can be first pushed up towards the uterine fundus to sound (measure the depth of) the uterine cavity, as shown with box 211.

Figure 8:
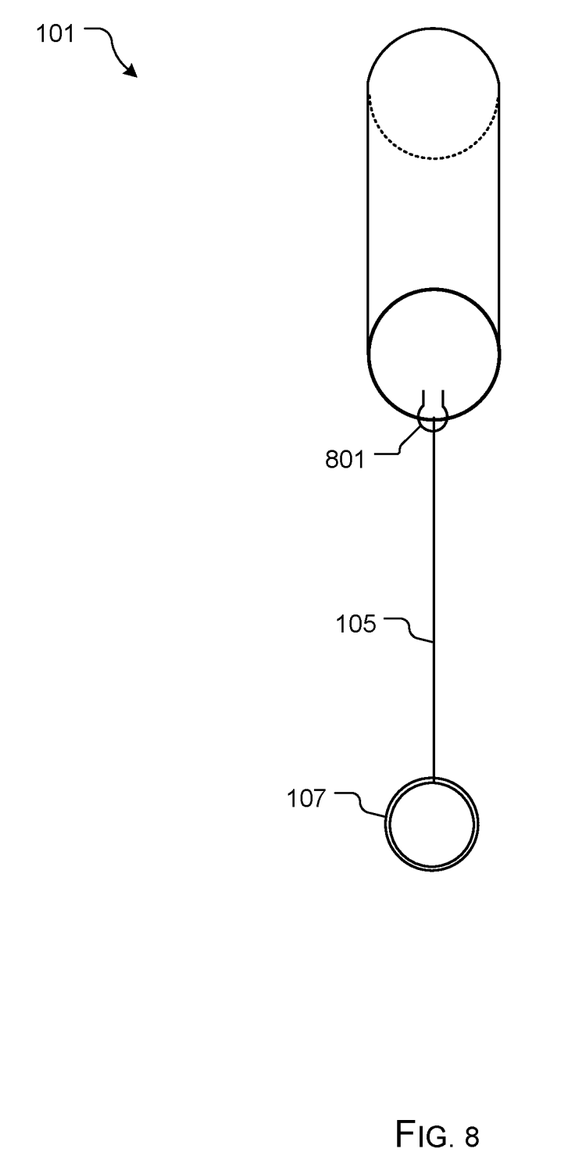
FIG. 8 is a front view of the dilator of FIG. 1 with a locking clip mechanism for the string in accordance with the present invention.

The string can be made of metallic material not limited to nitinol with a blunt tip 111 and measuring lines along the length of it. The string is attached to the tubular member in neutral position with the help of a locking clip 801 situated at the distal posterior midline of the tubular member. By unlocking the string (simply pulling it out of the lock), it becomes free to move inside the tubular member up towards the inside of the uterine cavity (or rectum or bladder) or downward releasing the metallic elastic wires into expansion.

It should be appreciated that the dimensions of the various components can vary as determined according to the targeted anatomical orifice (stricture) to dilate. For uterine cervix suggested dimensions (which can be adjusted according to results from clinical trials) and design of invention are 2-3 mm diameter at the tip and 10-12 mm diameter at the distal base where the handle and the string are attached with a to be determined length. The conical design allows a smaller proximal end to open strictures or closed anatomical passages otherwise meant to be open, like the uterine cervix (but also anal canal or urethra) non traumatic. Also allows the distal larger base to be handled by the user with ease.

Figure 3:
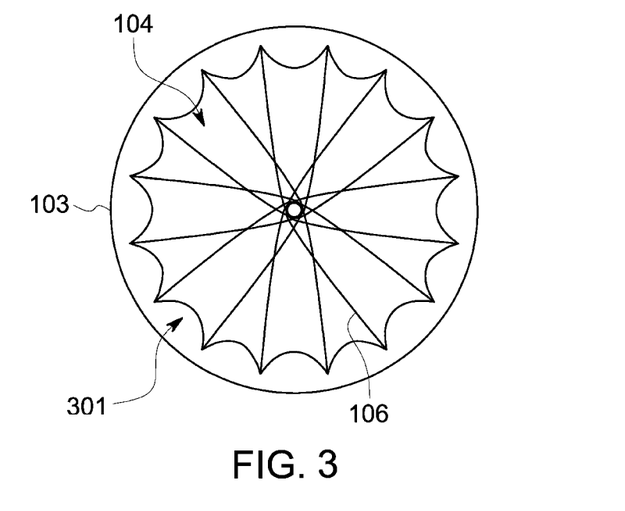
FIG. 3 is a cross sectional view taken from FIG. 1 in inactive, closed position.

Referring to FIG. 3, a cross sectional view taken from FIG. 1 at line 3, of the tubular member 103 is shown. The tubular member 103 can include a metallic core 301 that accommodates the plurality of elastic wires 106, which in some embodiments is composed of nitinol. The metallic core 301 and the elastic wires 106 can optional be made of any other materials (eg. Biodegradable) that fit the description of present embodiment, The wires 106 may be composed of very fine nitinol with a pre-determined tension strength and size such that when open, they release and expand at a pre-determined distance. (Young Modulus Factors). The tension strength can be progressively increased or decreased from tip of the invention to base such that in expanded position the invention assumes a cylindrical shape allowing free pass through of medical instruments.

In FIG. 3, the plurality of wires 106 are shown and are centered and held together by the string, when the invention is in the closed, inactivated position. The wires are equal distributed across the radius and length of the tubular member and overlap. In open, dilated, active position the wires recoil into a stretched curvilinear position which form the tubular structure with a pass-through opening.

In the preferred embodiment, the outer surface of the tubular member is made of highly compressed absorbent material which has a natural resiliency, and which when wet with fluid will tend to expand in an attempt to regain its initial shape without a strong adherence to the body tissues (similar to a "vaginal tampon material" as for example described in this patent A61F13/2051/U.S. Pat. No. 3,706, 311A). The outer, external surface of the invention, that comes in contact with the cervix is soft and has a smooth surface and can be provided with a plurality of pleats disposed around its cross-section that are capable of opening in an external direction (towards the cervix, pushing the cervix out into an open position) by the plurality of metallic wires when triggered (when removing the central string down and out of the cervix). The plurality of smooth outer pleats can be inverted to match with the plurality of inner elastic metallic wires. When the elastic wires are released and stretched to a dilated position, they will push the inverted plurality of the soft resilient outer material expanding them towards the anatomical orifice e.g. uterine cervix. The softer external material of the invention can potentially be medicated as needed or desired. The softer part of the invention may encompass a composite or a combination of materials.

Figure 4:
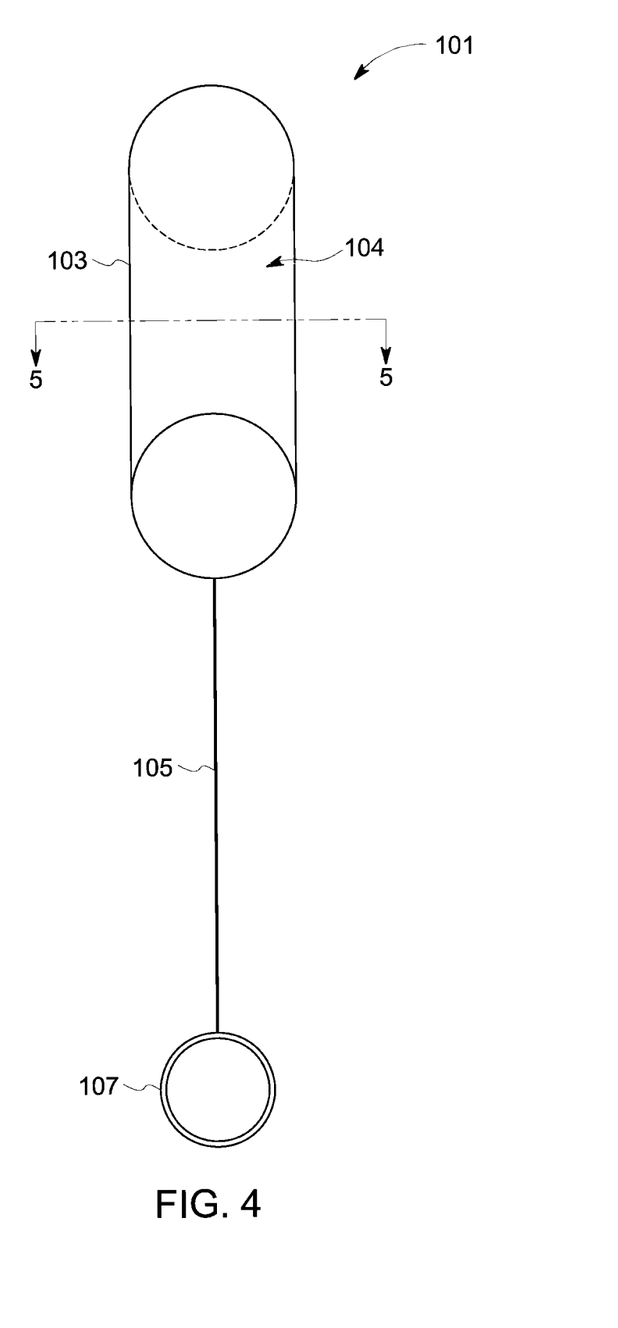
FIG. 4 is a front view of the dilator of FIG. 1 in a recoiled and dilated position.
Figure 5:
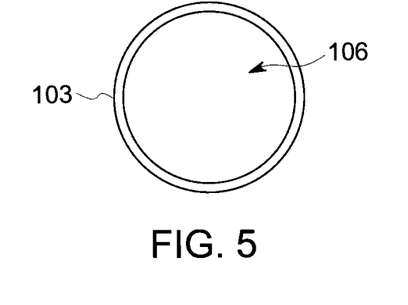
FIG. 5 is a cross sectional view taken from FIG. 4.

In FIGS. 4 and 5, the mechanism of pulling on the string 105 is shown. As shown, by pulling on the string, by the handle, the plurality of elastic wires 106 are released from inside of the tubular member and recoil to the outer surface expandable material to a predetermined dimension, dilating the cervical canal. The plurality of elastic wires, once released, pushes against the plurality of pleats of the expandable outer soft material with equally distributed forces. In the preferred embodiment, the string is made of metallic materials, nitinol, or reinforced blunt coil, although any desired materials may be used. In the preferred embodiment, the handle is attached to one (distal) end of the string and provides a circular structure (to allow a finger position and manipulation of device), although any desired design may be used.

In FIG. 5, a cross sectional view taken from line 5 of FIG. 4 shows the dilator in the dilated configuration, such that the channel 104 is open.

Figure 6:
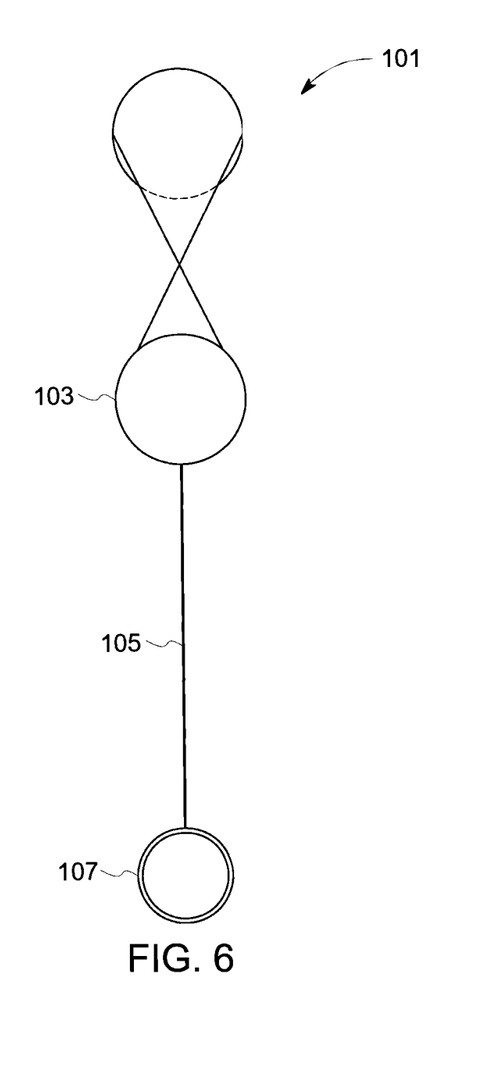
FIG. 6 is a front view of the dilator of FIG. 1 showing a twisting configuration.

As stated above, when the dilator 101 is in an open configuration, it allows for the free insertion of surgical devices. As shown in FIG. 6, the present invention can be twisted or crumpled from the base of the handle to 1. (Untwisted) Activate the device and release the string out of the elastic wires or to 2. (Twisted) Minimize size before insertion into cervix or before disposing and removal out of the cervical canal at the end of the procedure. Also, the invention can be extracted together with the hysteroscope or other medical device at the end of the procedure.

Figure 7:
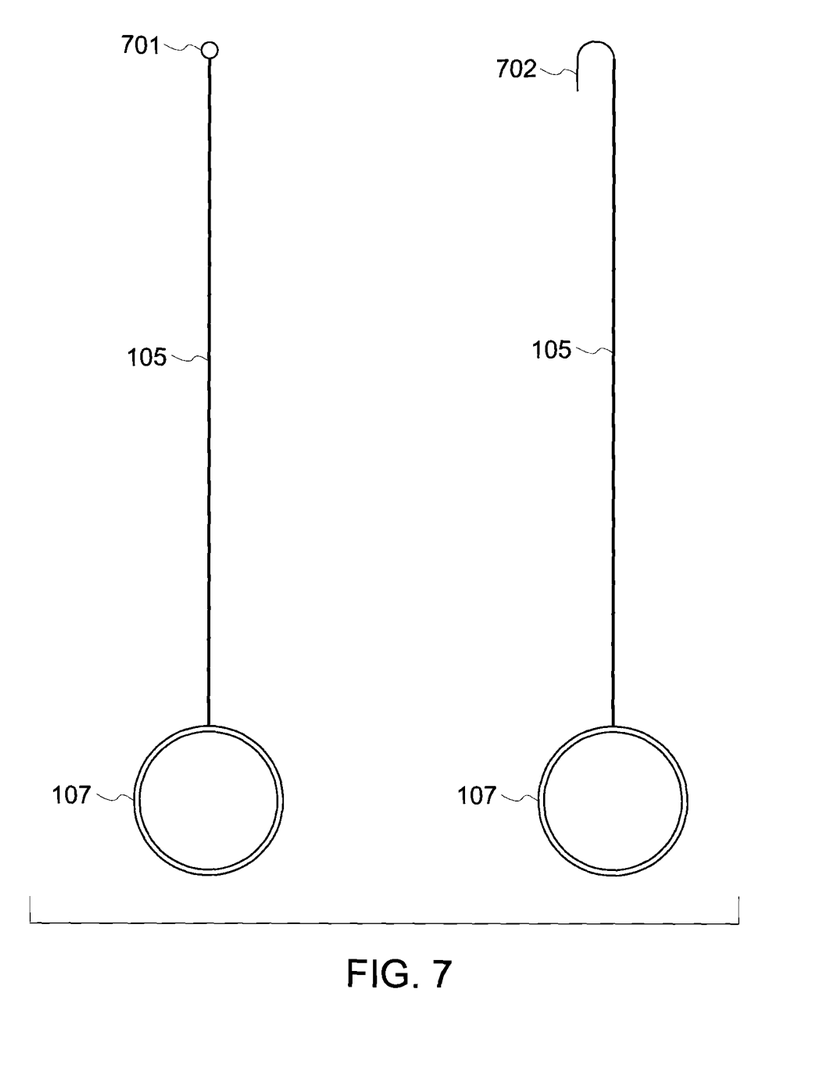
FIG. 7 shows two configurations of a handle and a string in accordance with the present invention.

In FIG. 7, the string 105 can also be a reinforced coil with a blunt proximal end 701, towards the uterine cavity, that can serve as an instrument to sound (measure) the uterus as it is first (pushed up and) unhooked from the metallic core. Then the string in the present invention, after measuring the uterine cavity (if necessary) is pulled down and out of cervical canal to release the plurality of elastic wires into the outer softer material to the expanded hollow tubular configuration. Once pulled out of the inner metallic core the string can be attached via a locking clip 801 to the base of the tubular expanded configuration, towards the distal end facing the outer cervix to allow manual control of the invention inside the cervical canal and uterus. In present embodiment the blunt proximal tip of the string (facing the inside of uterine cavity) can be designed as a hook 702 attached to the very last coil of metallic elastic tubular material; once the invention is manually triggered to open by untwisting the base of the distal part of the tubular component (base) and or pushing the string up, the tip of the string disengages from the elastic coil, to a straight upward position ready to pass up towards the uterine cavity for measurements or down through the elastic coils releasing them to an expanded, open tubular pass through dilated position. The tip of the string can very well be straight when the string is attached to the base by the locking clip. The shape and consistency of the tip of the string can encompass a multitude of forms and materials and is not limited to the description of present embodiment. The twisting of the base, distal part of the present invention, will allow compressing of the expanded tubular dilator, if needed at the end of the surgical procedure for removal and disposal. In present embodiment the tubular structure can appear twisted around the string in inactive compressed state and untwisted once the string is ready to be removed or already released out of the metallic coils into an active dilated position. Twisting of the tubular member around the string it is just a variant and not a mandatory part of the invention.

In FIG. 8, a front view depicts the dilator 101 having the string 105 supported by a locking clip 801. In the preferred embodiment the locking clip 801 is composed of a plastic but any other material can be used. The locking clip can contain the string by pushing in or release the string by pulling out.

The size and shape of the invention can be as depicted in FIG. 1 through 7, conical with one smaller end (minimal size 2-3 mm allowing passage through stenotic, closed cervix free of trauma) to be inserted into the cervix and an opposite larger base attached to the handle for hand instrumentation and advancement inside the cervix. (10-12 mm)

In present embodiment of the invention the string can be marked down from the tip all the way to the handle in inches or cm to allow precise measurements of the uterine cavity if such need is intended for the use of the invention.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A dilator configurable between a closed state for insertion into an anatomical orifice of a patient and an open state to form a passageway for a surgical device through the dilator and the anatomical orifice and into a cavity of the patient, the dilator comprising:
    a) a tubular member which is flexible: wherein in the closed state, the tubular member has a conical shape with a proximal end which is smaller than a base at a distal end opposite of the proximal end; and wherein in the open state, the tubular member has a cylindrical shape;
    b) a channel formed in the tubular member when in the open state and which provides the passageway which extends through the distal end and the proximal end of the tubular member; and wherein in the open state, the surgical device can pass through the passageway to enter into the cavity of the patient;
    c) a plurality of wires which form an inner metallic core inside of the tubular member; wherein the plurality of wires are equally distributed across a radius and a length of the tubular member and overlap with one another; and wherein in the closed state, the plurality of wires extend inwardly from an interior of the tubular member to a center of the tubular member;
    d) a string; wherein in the closed state, the string extends through the length of the tubular member and is engaged with and passed through a center of the plurality of wires thus holding them in the closed state such as to prevent recoiling into the open state; and
    e) a handle attached to the string;
        wherein pulling the handle away from the tubular member applies a force to the string;
        wherein the force to the string causes the string to disengage and release from the plurality of wires such that the plurality of wires recoil against and exert an outward force on the interior of the tubular member such that the tubular member expands from the closed state to the open state and takes on a diameter of a predetermined dimension, and in the open state
        the tubular member provides for dilation of a canal at the anatomical orifice; and
        wherein in the open state, the plurality of wires do not obstruct the channel so that the surgical device can pass therethrough.

2. The dilator of claim 1, wherein the string is of a metallic material, and is a reinforced blunt coil.

3. The dilator of claim 1, wherein an outer surface of the tubular member is composed of a soft, highly compressed, absorbent, coated material which has a natural resiliency, and which when wet with fluid will tend to expand in an attempt to regain its initial shape.

4. The dilator of claim 1, wherein the string includes a plurality of measuring lines so that the string can be used to measure the cavity; and
   wherein the plurality of measuring lines are marked from a tip of the string all the way to the handle.

5. The dilator of claim 1, wherein the tubular member has an outer external surface configured to come in contact with the anatomical orifice and the outer external surface is a smooth surface.

6. The dilator of claim 1, wherein an outer external surface of the tubular member includes a plurality of pleats formed therein and disposed around its cross-section which are configured to open in an external direction outward toward the anatomical orifice when triggered into the open state by the plurality of wires.

7. The dilator of claim 1, wherein the plurality of wires comprise Nitinol.

8. The dilator of claim 7, wherein the Nitinol has a pre-determined tension strength and size such that when the plurality of wires are opened, the plurality of wires release and expand at a pre-determined distance.

9. The dilator of claim 8, wherein the pre-determined tension strength is progressively increased or decreased from a tip of the dilator to the base of the dilator such that in the open state, the dilator assumes the cylindrical shape allowing free pass through of the surgical device.

10. The dilator of claim 1, wherein the string has a blunt tip at its proximal end opposite the handle.

11. The dilator of claim 1, wherein the plurality of wires recoil into a stretched curvilinear position when in the open state.

12. The dilator of claim 1, wherein the dilator includes a locking clip which retains the string engaged with the plurality of wires while in the closed state; and
   wherein the locking clip and the string are configured such that when the string is unlocked from the locking clip, the string is free to move inside the tubular member upward or downward.

13. A method of dilating a canal of an anatomical orifice to provide a passageway into a cavity of a patient, the method comprising:
   a) providing a dilator in a closed state, the dilator having:
      (i) a tubular member which is flexible and which has a conical shape in the closed state;
      (ii) a plurality of wires which form an inner metallic core inside of the tubular member, wherein the plurality of wires are equally distributed along a radius and a length of the tubular member, overlap with one another, and extend inwardly from an interior of the tubular member to a center of the tubular member;
      iii) a string which in the closed state extends through a length of the tubular member and is engaged with and passes through a center of the plurality of wires holding them in the closed state such as to prevent recoiling into an open state; and
      (iv) a handle attached to the string;
   b) inserting the tubular member into the canal; and
   c) pulling the handle away from the tubular member such as to apply a force to the string and causing the dilator to expand into the open state;
      wherein the force to the string causes the string to disengage from the plurality of wires such that the plurality of wires recoil against the interior of the tubular member such that the tubular member takes on a diameter of a predetermined dimension;
   wherein in the open state, the tubular member has a cylindrical shape and provides for dilation of the canal;
   wherein in the open state, a channel extends through a distal end and a proximal end of the tubular member such as to form the passageway through which a surgical device can pass through; and
   wherein in the open state, the plurality of wires recoil away from the center of the tubular member such as to expand the tubular member into the open state while not obstructing the channel.

14. The method of claim 13, wherein the method includes inserting the surgical device through the channel and into the canal.

15. The method of claim 13, wherein the string is comprised of a metallic material and is a reinforced blunt coil.

16. The method of claim 13, wherein an outer surface of the tubular member is composed of a soft highly compressed, absorbent, coated material which has a natural resiliency, and which when wet with fluid will tend to expand in an attempt to regain its initial shape.

17. The method of claim 13, wherein the string includes a plurality of measuring lines so that the string can be used to measure the cavity;
   wherein the plurality of measuring lines are marked from a tip of the string all the way to the handle; and
   wherein the method includes measuring the cavity with the string.

18. The method of claim 13, further comprising, removing the dilator at an end of a procedure by itself or together with medical instruments in block.

19. The method of claim 18, wherein the removing includes twisting the dilator at a base such that the tubular member is compressed.

20. A dilator configurable between a closed state for insertion into an anatomical orifice of a patient and an open state to form a passageway for a surgical device through the dilator and the anatomical orifice and into a cavity of the patient, comprising:
   a) a tubular member which is flexible; wherein in the closed state, the tubular member has a conical shape with a proximal end which is smaller than a base at a distal end opposite of the proximal end; and wherein in the open state, the tubular member has a cylindrical shape;
   b) a channel formed in the tubular member when in the open state and which provides a passageway which extends through the distal end and the proximal end of the tubular member; and wherein in the open state, the surgical device can pass through the passageway to enter into the cavity of the patient;
   c) a plurality of wires comprising Nitinol and which form an inner metallic core inside of the tubular member; wherein the plurality of wires are equally distributed across a radius and a length of the tubular member and overlap with one another; wherein in the closed state, the plurality of wires extend inwardly from an interior of the tubular member to a center of the tubular member;
   d) a string which comprises a reinforced blunt coil; wherein in the closed state, the string extends through the length of the tubular member and is engaged with and passes through a center of the plurality of wires thus holding them in the closed state such as to prevent recoiling into the open state;
   e) a handle attached to the string;

wherein pulling the handle away from the tubular member applies a force to the string;

wherein the force to the string causes the string to disengage and release from the plurality of wires such that the plurality of wires recoil against and exert an outward force on the interior of the tubular member such that the tubular member expands from the closed state to the open state such that the tubular member is configured to provide for dilation of a canal at the anatomical orifice; and wherein in the open state, the plurality of wires do not obstruct the channel so that the surgical device can pass therethrough.

* * * * *